(12) United States Patent
Pfistershammer

(10) Patent No.: US 7,455,968 B2
(45) Date of Patent: Nov. 25, 2008

(54) DETECTION METHOD

(75) Inventor: Josef Pfistershammer, Claremont (AU)

(73) Assignee: ID+PLUS Ltd., West Perth (AU)

( * ) Notice: Subject to any disclaimer, the term of this patent is extended or adjusted under 35 U.S.C. 154(b) by 175 days.

(21) Appl. No.: 10/381,715

(22) PCT Filed: Oct. 3, 2001

(86) PCT No.: PCT/AU01/01246

§ 371 (c)(1),
(2), (4) Date: Oct. 8, 2003

(87) PCT Pub. No.: WO02/29085

PCT Pub. Date: Apr. 11, 2002

(65) Prior Publication Data
US 2004/0072247 A1 Apr. 15, 2004

(30) Foreign Application Priority Data
Oct. 3, 2000 (AU) .................. PR0507

(51) Int. Cl.
C12Q 1/68 (2006.01)
C12P 19/34 (2006.01)
C07H 21/02 (2006.01)
C07H 21/04 (2006.01)
C07H 21/00 (2006.01)

(52) U.S. Cl. .................. 435/6; 435/91.1; 435/91.2; 536/23.1; 536/24.3; 536/24.33; 536/25.3; 536/25.32

(58) Field of Classification Search ............ 435/6, 435/91.1, 91.2, 183, 283.1, 287.1, 287.2; 436/94; 536/23.1, 24.3, 24.33, 25.3, 25.32
See application file for complete search history.

(56) References Cited

U.S. PATENT DOCUMENTS

| | | | | |
|---|---|---|---|---|
| 5,391,480 | A | | 2/1995 | Davis et al. |
| 5,658,749 | A | * | 8/1997 | Thornton ............... 435/29 |
| 5,922,617 | A | * | 7/1999 | Wang ................. 436/518 |
| 6,083,698 | A | * | 7/2000 | Olson et al. ............ 435/6 |
| 6,159,693 | A | | 12/2000 | Shultz et al. |
| 6,210,891 | B1 | | 4/2001 | Nyren et al. |
| 6,210,894 | B1 | | 4/2001 | Brennan |
| 2002/0142336 | A1 | | 10/2002 | Smith et al. |

FOREIGN PATENT DOCUMENTS

| | | | |
|---|---|---|---|
| EP | 0 223 618 | A2 | 5/1987 |
| EP | 0 587 298 | A2 | 3/1994 |
| EP | 0 587 298 | A3 | 3/1994 |
| EP | 0 919 565 | A2 | 6/1999 |
| EP | 0 919 565 | A3 | 6/1999 |
| WO | WO 89/09283 | A1 | 10/1989 |
| WO | WO 93/23564 | A1 | 11/1993 |
| WO | WO 98/13523 | * | 4/1998 |
| WO | WO 98/48046 | * | 10/1998 |
| WO | WO 99/46409 | A1 | 9/1999 |
| WO | WO 00/49179 | A1 | 8/2000 |
| WO | WO 00/49182 | A2 | 8/2000 |
| WO | WO 00/60121 | A1 | 10/2000 |
| WO | WO 01/62975 | A2 | 8/2001 |

OTHER PUBLICATIONS

Marquez, Nov. 1996, J. Biol. Chem., vol. 271, pp. 28903 and 28911.*
Bi, 1998, Nucleic Acids Res., vol. 26, pp. 3073-3075.*
Attached definition for single nucleotide polymorphism.*
Marquez, L.A., et al., "Using 2-Aminopurine Fluorescence and Mutational Analysis to Demonstrate an Active Role of Bacteriophage T4 DNA Polymerase in Strand Separation Required for 3'-5'-Exonuclease Activity", *The Journal of Biological Chemistry*, vol. 271, No. 46, Issue of Nov. 15, pp. 28903-28911, 1996.
Morin, P.A., et al., Research Report: "High-Throughput Single Nucleotide Polymorphism Genotyping by Fluorescent 5' Exonuclease Assay", *BioTechniques*, vol. 27, No. 3, pp. 538-552, Sep. 1999.
Täpp, I., et al., Research Report: "Homogeneous Scoring of Singe-Nucleotide Polymorphisms: Comparison of the 5'-Nuclease Taq-Man® Assay and Molecular Beacon Probes", *BioTechniques*, vol. 28, No. 4, pp. 732-738, Apr. 2000.
Bi, W., et al., "Detection of Known Mutation by Proof-reading PCR", *Nucleic Acids Research*, 1998, vol. 26, No. 12, 3073-3075.
Wegmuller, B., et al., "3'-5' Proofreading-induced detection of piont mutations by PCR using Tli DNA polymerase", *Nucleic Acids Research*, 1995, vol. 23, No. 2, 311-312.
Tabor, S., et al., "DNA sequence analysis with a modified bacteriophage T7 DNA polymerase", *Journal of Biological Chemistry*, 265:14 (May 15, 1990), 8322-8328.

* cited by examiner

*Primary Examiner*—Frank W Lu
(74) *Attorney, Agent, or Firm*—Rothwell, Figg, Ernst & Manbeck, P.C.

(57) ABSTRACT

A method of identifying a base at a target position in a single-stranded sample DNA sequence, the method characterised by the steps of: (i) providing an oligonucleotide probe which is capable of hybridising to the sample DNA sequence such that the 3' nucleotide of the probe overlaps the target position, the probe being blocked at the 3' end to prevent extension by DNA polymerase but permitting 3'-5' exonuclease cleavage; (ii) incubating the sample DNA sequence with the probe in the presence of (a) a composition having 3'-5' exonuclease activity and (b) nucleotide triphosphates, under conditions that allow hybridisation of the probe to the sample DNA sequence; and (iii) detecting, directly or indirectly, cleavage of the 3' nucleotide of the probe.

11 Claims, 3 Drawing Sheets

| | | | | |
|---|---|---|---|---|
| Probe set 1 | ...A | ...C | ...T | ...G |
| Probe set 2 | ..A | ..C | ..T | ..G |
| Probe set 3 | ..A | ...C | .T | ..G |
| Probe set 4 | ..A | ..C | ..T | ..G |
| - | | | | |
| - | | | | |
| - | | | | |
| - | | | | |
| Probe set 1 | ...A | ..C | ...T | ...G |
| Probe set 2 | ..A | ..C | ..T | ..G |
| Probe set 3 | ..A | ...C | ..T | ..G |
| Probe set 4 | ..A | ..C | ..T | ..G |

"..." represent the rest of the probe sequence and differs between probe sets 1, 2, 3 and 4

Fig. 2.

DETECTION METHOD

CROSS REFERENCE TO RELATED APPLICATIONS

This application is a 35 U.S.C. §371 National Phase entry application from PCT/AU01/01246, filed Oct. 3, 2001 and designating the United States.

FIELD OF INVENTION

The present invention relates to a detection method. More particularly, the detection method of the present invention is intended for use in identifying single bases, in particular single nucleotide polymorphisms (SNP's).

BACKGROUND ART

The ability to detect and quantify nucleic acid polymorphisms is useful in the characterising of individual animals, humans, plants and other organisms. In particular, it is desirable to detect a difference in a nucleic acid polymorphism to distinguish between individuals.

Methods for determining the presence of nucleic acid target sequences, in particular a base at a target position in a sample of DNA are known. One such method is to separate DNA fragments of interest in a sample by methods such as agarose or acrylamide gel electrophoresis and hybridise a labeled oligonucleotide probe to a nucleic acid sequence in a sample or on a blot (Southern blotting) and to then detect the presence of the hybridised probe via the label. Generally the label is a radioactive material, fluorescent dye or enzyme such as horseradish peroxidase, urease or alkaline phosphatase.

Another method for the detection of the hydridised probe and nucleic acid sequence is the use of polymerase chain reaction (PCR) techniques. This method requires the use of two (2) oligonucleotides, the PCR primers. These PCR primers are annealed to the target sequence in a cyclic manner and the DNA polymerase reaction extends the DNA duplex from the primers resulting in the amplification of the region between the primers. The absence of a PCR product indicates that hybridisation of one or both primers did not occur. Detection of the PCR product may be achieved in similar ways as described above, although methods are available that rely on non-gel detection, such as molecular beacons and TaqMan® 5'-3' exonuclease chemistry (see for example U.S. Pat. Nos. 5,119,801, 5,312,728, 5,691,146; 5,723,591; 5,691,146; 5,876,930; and associated instrumentation). Other methods are available to detect the presence of hybridised oiigonucleotides to specific DNA sequences.

Many of these presently available methods require the use of expensive or potentially hazardous reagents, such as radioactive materials and fluorescently labeled oligonucleotides. In addition, many of the methods are time consuming and involve many steps that may ultimately reduce the accuracy and/or sensitivity of the method applied. As a consequence, the majority of these methods are poorly suited to the field of livestock SNP mass screening.

Other methods available utilise the proofreading capacity of DNA polymerases. Methods of determining the presence or absence of a predetermined nucleic acid target sequence in a nucleic acid sample using this proofreading activity are in part described in International Publication WO 00/49179 and International Publication WO 00/49182. One method described in these publications utilises a depolymerase enzyme that depolymerises nucleic acid from the 3'-terminus of an oligonucleotide probe hybridized to a nucleic acid target sequence via the process of pyrophosphorolysis and measures the subsequent release of one or more nucleotide triphosphates. In a second method described, the exonuclease activity of DNA polymerase is used to remove mismatched nucleotides from the 3' end of a probe. To minimise the background present in the detection step of the method the hybridised probe/sample complex is purified from the remaining oligonucleotide.

The 3'-5' exonuclease activity of DNA polymerases has been intensively studied since the late 1980's and it is known that this activity increases the accuracy of DNA replication over DNA polymerisation alone (Morales J C and Kool E T (2000) *Biochemistry* 39(10): 2626-32; Lam W C, Van der Schans E J, Joyce C M, Millar D P (1998) *Biochemistry* 37(6): 1513-22; Das S K and Fujimura R K (1980) *Nucleic Acids Research* 8(3): 657-71; Baker R P and Reha-Krantz L J (1998) *Proc. Natl. Acad. Sci U.S.A* 95(7): 3507-12; Canard b, Cardona B, Sarfati R S (1995) *Proc. Natl. Acad. Sci U.S.A* 94(24): 10859-63; de Vega M, Lazaro J M, Sala M, Blanco I (1996) *EMBO J* 15(5): 1182-92; Goodman M F, Creighton S, Bloom L B, Petruska J (1993) *Crit Rev Biochem Mol Biol* 28(2): 83-126; Johnson K A (1993) *Annu Rev Biochem* 62: 685-713; Thomas K R and Baldomero M O (1978) The *Journal of Biological Chemistry* 253(2): 424-429; Perler F B, Kumar S, Kong H (1996) *Advances in Protein Chemistry* 48: 377435.

However, the steps involved in proofreading by the 5'-3' exonuclease activity are not well defined. Marquez L A and Reha-Krantz L J (1996) *J Biol Chem.* 271(46): 28903-11, studied the biochemical characteristics of a mutant T4 DNA polymerase to determine its role in strand separation. Using a mutant T4 DNA polymerase, together with the subsequent release of fluorescent d2APMP as a detection system, the molecular details of the 3'-5' exonuclease activity of the T4 DNA polymerase were determined.

Using this method Marquez & Reha-Krantz were able to show how DNA with a single terminal mismatch was converted into a substrate for the hydrolysis reaction. From this study it was possible to determine the rate limiting steps required to prepare the DNA for the excision reaction. The researchers' findings showed the proofreading pathway in which DNA is first transferred from the polymerase active center to a pre-exonuclease complex and then further processed to produce the partially single-stranded DNA required for the hydrolysis reaction.

The present invention seeks to provide a low cost, high throughput detection system for identifying and characterizing individual animals on the basis of differences in individual nucleotides at particular positions in the genome (i.e. single nucleotide polymorphisms (SNPs)). It differs from and improves upon the previous methods which utilize the 3'-5' exonuclease activity of DNA polymerases and other suitable exonucleases. Without exception, the prior methods rely on the use of DNA probes which can be also be used as DNA primers in PCR (referred to in International Publication WO 00/49179 and International Publication WO 00/49182 as primers). The method of the present invention requires rather that the oligonucleotide probes hybridised to the sample are not able to be extended by the action of a DNA polymerase during the cleavage stage of the reaction and cannot therefore be considered as primers for PCR. To this end the oligonucleotides are blocked at the 3' end by the use of phosphate, dideoxy or other moieties that prevent extension of the oligonucleotide probe by the polymerase in the reaction. This distinction has the benefit that the method reaction can be carried out without the need for prior purification of the oligonucleotide probe/sample duplex as the polymerization reaction is prevented unless cleavage of the blocking 3' nucleotide has occurred.

The main purpose of utilising this protocol and technology is its ability to lower the cost of individual ID tests, a very necessary feature for applications within livestock industries where mass screenings are generally the aim.

The preceding discussion of the background art is intended to facilitate an understanding of the present invention only. It should be appreciated that the discussion is not an acknowledgement or admission that any of the material referred to was part of the common general knowledge in Australia as at the priority date of the application.

Definitions

To facilitate understanding of the present invention, a number of terms are defined below.

A "probe" as used herein refers to an oligonucleotide or polynucleotide sequence which is able to hybridise to a sample DNA sequence under low stringency conditions, and which is blocked at the 3' end such that it cannot be extended by DNA polymerases but is able to act as a substrate for the 3'-5' proofreading exonuclease activity of DNA polymerases.

A "primer" as used herein refers to an oligonucleotide or polynucleotide sequence which is able to hybridise to a sample DNA sequence under low stringency conditions, and which can be extended by DNA polymerases with the concomitant release of pyrophosphate.

Throughout this specification, unless the context requires otherwise, the word "comprise", or variations such as "comprises" or "comprising", will be understood to imply the inclusion of a stated integer or group of integers but not the exclusion of any other integer or group of integers.

DISCLOSURE OF THE INVENTION

In accordance with the present invention there is provided a method of identifying a base at a target position in a single-stranded sample DNA sequence, the method characterised by the steps of:

(i) (i) providing an oligonucleotide probe which is capable of hybridising to the sample DNA sequence such that the 3' nucleotide of the probe overlaps the target position, the probe being blocked at the 3' end to prevent extension by DNA polymerase but permitting 3'-5' exonuclease cleavage;

(ii) incubating the sample DNA sequence with the probe in the presence of (a) a composition having 3'-5' exonuclease activity and (b) nucleotide triphosphates, under conditions that allow hybridisation of the probe to the sample DNA sequence;

(iii) detecting, directly or indirectly, cleavage of the 3' nucleotide of the probe.

In a preferred embodiment, the 3'-5' activity of the composition is provided by a DNA dependant DNA polymerase with proofreading 3'-5' nuclease activity. The 3' nucleotide of the probe is terminally blocked so as to prevent extension of the un-cleaved probe by a DNA polymerase enzyme in the event the 3' nucleotides are mismatched the 3'-5' exonuclease activity of the polymerase will cleave the terminal mismatched nucleotide generating a free 3' end suitable for the action of the DNA polymerase and step (iii) comprises detecting the formation of pyrophosphate produced by extension of the cleaved probe by a DNA polymerase in the event that the 3' termini are mismatched.

In an alternative embodiment, the 3' blocked oligonucleotide probe also comprises a fluorescent moiety and a quencher moiety, the fluorescent moiety or the quencher moiety, but not both, being attached to the 3' nucleotide of the probe, and step (iii) comprises detecting an increase in fluorescence following 3'-5' exonuclease cleavage of the probe.

In an alternative embodiment an oligonucleotide probe is hybridised with sample DNA such that the 3' end of the probe overlaps the target position. In the event of a 3' mismatch the 3'-5' proofreading activity of the DNA polymerase will cleave the mismatch. Another, 3' blocked oligonucleotide probe comprising a fluorescent moiety and a quencher moiety, the fluorescent moiety or the quencher moiety, but not both, being attached to the 3' nucleotide of the probe is simultaneously hybridised to the sample less than about 500 nucleotides downstream of the previous probe on the same strand of DNA, and step (iii) comprises cleavage of the 3' mismatch followed by polymerisation from the resultant primer and concomitant 5'-3' exonuclease cleavage of the downstream probe and detection of increased fluorescence.

Preferably, the detection of pyrophosphate comprises contacting the pyrophosphate with a means for converting pyrophosphate to adenosine triphosphate (ATP) and detecting the presence of ATP. Typically, the ATP is detected by contacting the ATP with means for hydrolysing ATP with concomitant production of light. The light is typically detected by optical means.

Two or more probes may be provided which hybridise to the same location in the sample DNA sequence and which have a different base at the 3' end.

Two or more probes may be provided which hybridise to the same location in the sample DNA sequence and which have a different base at the 3' end.

Typically, the target position represents a single nucleotide polymorphism and different probes are provided which have a 3' nucleotide complementary to each of the possible polymorphisms and which hybridise to the same location in the sample DNA sequence.

In a preferred embodiment, the probe or probes are immobilised to a solid phase. Preferably, a plurality of probes are provided for the identification of a plurality of target positions, each different probe being provided in a discrete location on the solid phase. More preferably, each probe is provided at a plurality of positions on the solid phase.

In an embodiment suited to automation of the detection method of the present invention, the probes may be provided as a discrete array on a solid phase and the array is moved relative to the means for detecting the cleavage of the 3' nucleotide of any probe in a continuous or semi-continuous manner.

The use of a DNA probe in a method of identifying a base at a target position in a single-stranded sample DNA sequence characterised in that the probe is hybridised to said sample DNA sequence such that the 3' nucleotide of the probe overlaps the target position, the 3' nucleotide of the probe being terminally blocked so as to prevent primer extension by a DNA polymerase enzyme, whereas if there is a mismatch between the nucleotides at the target position the mismatched 3' nucleotide of the probe is cleaved thereby exposing bases in the probe suitable for primer extension, producing pyrophosphate which is subsequently detected.

In accordance with the present invention there is still further provided a kit comprising a plurality of DNA probes for use in the identification of a nucleotide base at a plurality of target positions in a single stranded DNA ample, characterised in that each probe is capable of hybridising to the ample DNA sequence such that the 3' nucleotide of the probe overlaps a The kit may further comprise a composition having a 3'-5' exonuclease activity, and optionally a DNA polymerase enzyme and/or a reagent capable of converting the formation of pyrophosphate into an optically detectable signal.

In a further aspect the present invention provides an apparatus for use in the above method of the invention, characterised in that the apparatus comprises:
(i) A detection device for detecting an optical change at one or more discrete positions on a film, said film being moved relative to the detection device in a unidirectional continuous or semi-continuous manner;
(ii) A device for moving the film relative to the detection device; and
(iii) One or more devices for applying nucleotide extension primers and/or reagents at discrete positions on the film prior to, or concomitant with, the detection of an optical change at those positions.

BRIEF DESCRIPTION OF THE DRAWINGS

The present invention will now be described, by way of example only, with reference to the accompanying drawings, in which:

FIG. 2 is a diagrammatic representation of the arrangement of probes on a solid phase in accordance with the present invention.

BEST MODE(S) FOR CARRYING OUT THE INVENTION

Sample nucleic acids for use in the detection methods of the present invention are typically genomic DNA obtained using standard techniques. However, other types of nucleic acid may be used. Preferably the genomic DNA is obtained from a mammal such as a human or domestic or farm animals such as dogs, cats, pigs, sheep, cows and goats. The nucleic acid may be single or double stranded.

The probes will typically be DNA probes. Probes may be of any length but are preferably at least 10, 15, 20, 30, 40 or 50 nucleotides in length, more preferably less than 1000, 500 or 200 nucleotides in length. Probes may comprise modified bases.

Figure 1:
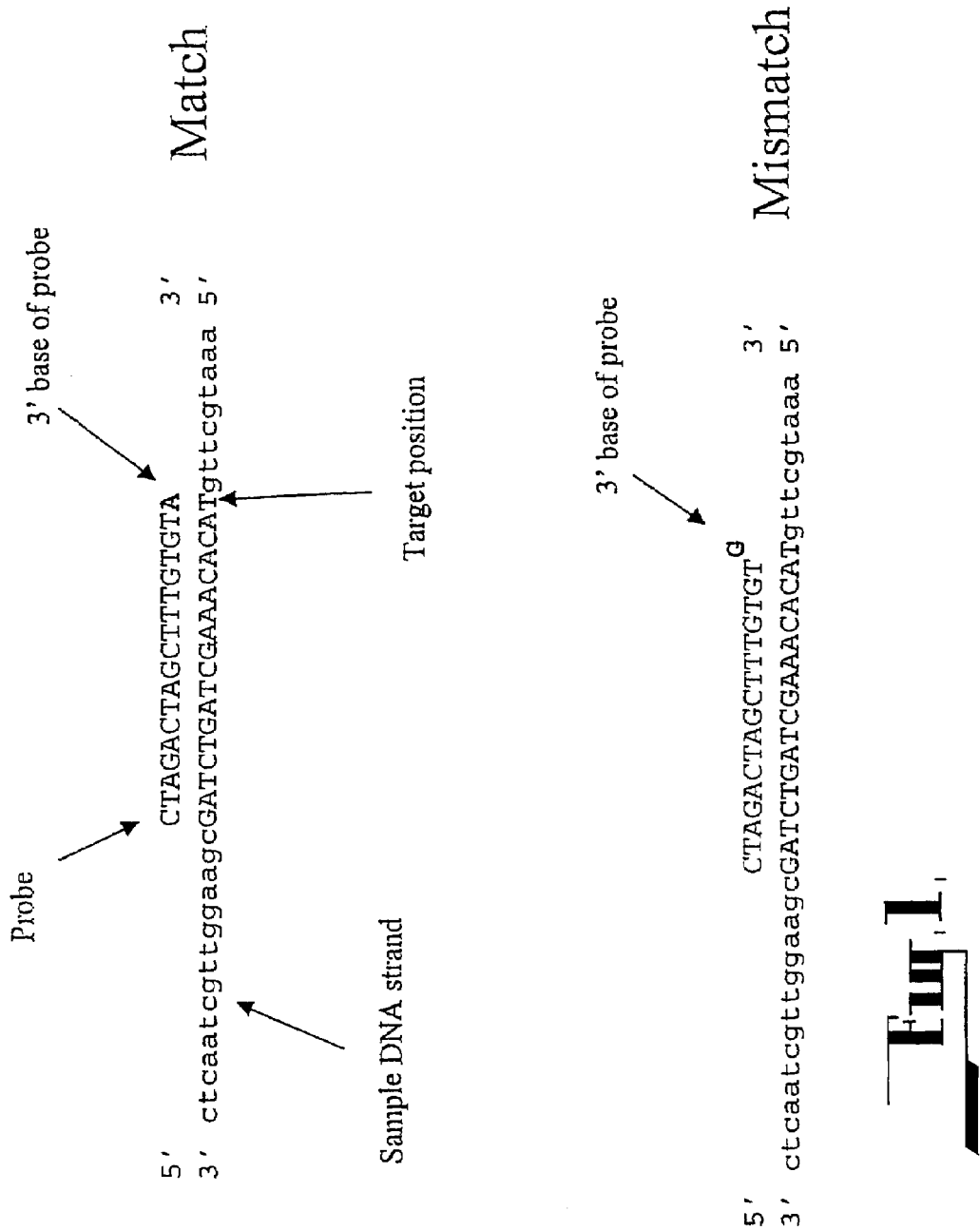
FIG. 1 is a diagrammatic representation of the principles of the 3'- 5' exonuclease detection method of the presention invention 5'-aaatgcttgtacacaaagctagtctagcgaagttgctaactc-3' [SEQ ID NO: 1], 5'-ctagactagctttgtgta-3'[SEQ ID NO: 2], 5'-ctagactagctttgtgtg-3'[SEQ ID NO: 3].

The nucleotide sequence of the probes is selected so that they selectively hybridise to a selected region of a sample DNA. More specifically, the sequence of the probes is chosen such that when the probe hybridises to the sample DNA, the 3' end of the probe overlaps a target base position in the sample DNA (see FIG. 1). In this way, if the base at the 3' end of the probe is complementary to the base at the target position then they will base pair, if not then the 3' end of the probe will form a mismatch.

Preferably, the probe is selected such that it only anneals to a unique region of the genome of a given organism and not to other regions of that same genome under selective conditions. Furthermore, the target position in that region is typically polymorphic such that the nucleotide base at that position varies between individuals of the same species, i.e. represents a single nucleotide polymorphism (SNP). SNPs may be diallelic (two different forms), triallelic (three different forms) or exist as all four possible forms. However, for the purpose of identification based upon SNPs, only diallelic forms are considered.

The method of the invention is based on the ability of certain enzymes to recognise mismatches between otherwise complementary double-stranded nucleic acids and remove the mismatched bases. Consequently, in the method of the present invention, if the 3' terminal base of the probe is not complementary to the base it overlaps on the sample DNA then these enzymes will cleave off the 3' terminal base of the probe.

The method of the invention therefore involves incubating the probe with single stranded sample nucleic acids (or denatured double stranded sample nucleic acids)-under conditions that allow the probe to hybridise selectively to the target nucleic acid. If the 3' end of the probe is not complementary to the corresponding base in the sample nucleic acid, then the resulting mismatch is cleaved by contacting the probe/sample nucleic acid duplex with a composition that is capable of cleaving a mismatch. This may be achieved by chemical means but is more preferably achieved by using a 3'-5' exonuclease enzyme, such as the proofreading 3'-5' exonuclease activity of certain DNA dependant DNA polymerases. When an enzyme is used, unless the hybridised probe/sample DNA nucleic acid duplex is purified prior to subsequent steps in the reaction, it is necessary to include deoxynucleotide triphosphates (dNTPs) in the reaction mix because the exonuclease reaction will proceed to some extent even if no mismatch is present in the absence of dNTPs resulting in cleavage of the oligonucleotide probe without the requirement for 3' mismatch hybridisation. Also in the absence of dNTP's the unbound probe may also be cleaved leading to the release of pyrophosphate and leading to increased background.

The next step in the detection method is to detect this cleavage event. In one embodiment, the 3' terminal base of the blocked oligonucleotide probe is labelled with a fluorescent molecule and another part of the probe is labelled with a quencher (or vice versa). When the 3' base in cleaved, the fluorescent molecule is separated from the quencher and is able to give an increase in the fluorescent signal. This type of detection technology is described for a polymerase chain reaction (PCR) procedure in Livak, Genet Anal., 1999, 14: 143. If no cleavage takes place then no increase in fluorescence is seen.

Alternatively, the cleavage event can be detected using pyrophosphate methodologies. Essentially, the 3' base of the probe is "blocked" such that, although the probe is annealed to a complementary nucleic acid, 5'-3' primer extension in the presence of a DNA polymerase enzyme and dNTPs cannot take place. Suitable nucleotide chemistries are known in the art to produce 3' blocked nucleotides.

However, if the 3' base is cleaved, the other bases in the probe are suitable for primer extension and the DNA polymerase will proceed to synthesise a complementary strand in a 5'-3' direction, extending the resultant primer. This will result in the production of pyrophosphate. The production of pyrophosphate can be detected by a variety of methods. One suitable method includes the use of ATP sulfurylase and firefly luciferase (Nyren, 1987, Anal. Biochem. 167: 235). These comprise a means of converting pyrophosphate to ATP, the ATP being hydrolysed by the luciferase to produce light.

The cleavage event is typically detected by optical means such as using a charge coupled device (CCD), e.g. a digital camera. The image generated by the optical means is typically processed by a computer loaded with suitable software to convert the image generated by the optical means into meaningful information.

Thus, the method of the invention essentially determines whether the 3' end base of a probe annealed to a sample nucleic acid and the base it overlaps in a target position in the sample nucleic acid are the same or different.

In the case of diallelic polymorphisms, it is only necessary to use one probe to determine the base at a target position. For example, if the polymorphism is T or G and a probe is provided with a C at the end, DNA from individuals with a G at the target position will anneal perfectly at the 3' end of the probe and no cleavage event will occur. However, nucleic acid from individuals with a T at the target position will not anneal properly at the 3' end of the probe and a mismatch will occur. This mismatch can be cleaved selectively and the cleavage event detected.

Two probes, one with a C and one with an A at the end may be used to provide a control since in these circumstances at least one probe or the other should generate a cleavage event.

In the case of triallelic polymorphisms or polymorphisms where all four bases are possible, it is necessary to use two, three or four different probes. The probes will typically be identical except for a different 3' base but variation in other parts of the probe are tolerated if the resulting probe still hybridises selectively to the same region of a genome as the other probes.

Where groups of probes are used to detect an individual polymorphism, they will typically be provided in discrete reactions. For example, the probes may be immobilised to a solid phase such as glass slide and the related probes grouped together (see FIG. 2).

Generally, it is preferred to immobilise the probes to a solid phase. Suitable solid phases include microtitre wells, derivatised glass, silicon or plastics. In one embodiment, the solid phase is a film, preferably a film that can be wound onto a reel. Preferably the probes are provided as an array, more preferably an array that can be moved in a continuous or semi-continuous manner in relation to the optical detection means (although the optical detection means could be moved relative to the array).

Thus, for example, the probes may be provided on a solid phase that can be placed in an X-Y reader machine. In a particularly preferred embodiment, the probes are provided on a thin film that is moved in a continuous or semi-continuous manner in relation to the optical detection means.

Figure 3:
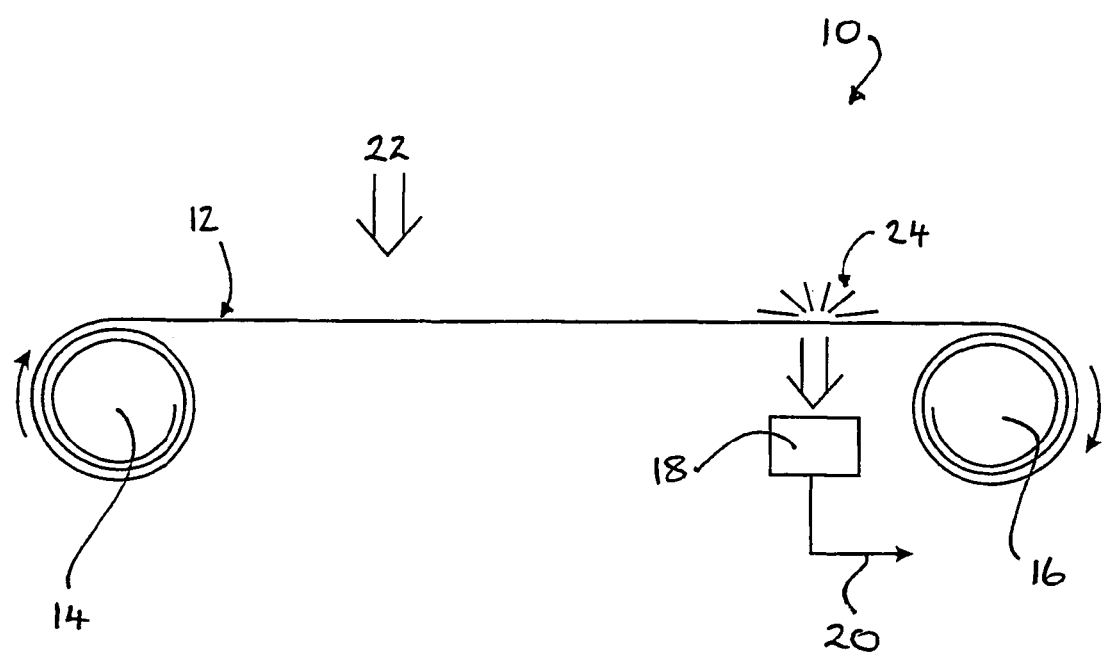
FIG. 3 is a diagrammatic representation of an apparatus for carrying out the method of the present invention.

The probes may be pre-immobilised to the solid-phase prior to being used in the detection method or they may be continuously applied to the solid phase immediately prior to the addition of other components of the reaction and being read by the optical detection means. See, for example, FIG. 3 where a robot is used to spot probes onto a film which is then advanced to another robot which adds DNA samples and reagents. The film is then advanced over the detection means, a CCD camera.

To enhance reliability and reproducibility, it is preferred to use each probe more than once in a test. Preferably each individual probe is applied to the solid phase in at least a duplicate and more preferably at different locations on the solid phase in triplicate form.

Annealing of probes to sample nucleic acids and subsequent reaction and detection steps need not be performed with the probes in the solid phase. However, especially in the context of automation, immobilisation is preferred.

Generally, a range of probes are used that detect different target base positions. For the purposes of genetic identification it will be necessary to use enough probes such that within a test population, individuals can be unambiguously identified. Preferably, at least 40 groups of probes are used, more preferably at least 60 groups of probes. A group of probes is meant to refer to probes that hybridised to predetermined positions in a genome but which may comprise a different 3' end base.

The probes may be provided as a kit, for example with a range of probes that hybridise selectively to different parts of a genome. Kits may include means for cleaving 3' end mismatches, a DNA polymerase, dNTPs, means for converting pyrophosphate to ATP and means for hydrolysing ATP with concomitant generation of light. Kits may also comprise instructions for use and suitable packaging.

An apparatus 10 for use in the present invention typically comprises a detection device for detecting an optical change at one or more discrete positions on a film, said film being moved relative to the detection device in a unidirectional continuous or semi-continuous manner. Examples of devices include CCDs (such as digital cameras).

The apparatus 10 also typically comprises a device for moving the film relative to the detection device. Thus in one embodiment, shown in FIG. 3, a film 12 is provided on a motorised supply reel 14. A free end of the film 12 is attached to a take-up reel 16, which is also motorised. The motors serve to advance the film 12 from the supply reel 14 to the take-up reel 16. A detection device 18 is typically mounted underneath the film 12, although it could be mounted above the film. When the detection device 18 is mounted below the film they should be at least partially capable of allowing a light signal generated on top to be read from below (i.e. be translucent or transparent). Signals from the detection device 18 are passed to an image processor 20.

The apparatus also typically comprises one or more devices 22 for applying nucleotide extension primers and/or reagents at discrete positions on said film prior to, or concomitant with, the detection of an optical change 24 at said positions. Devices, such as robots, for applying reagents etc. to solid phases are widely known.

The present invention will now be described with reference to a number of examples which are to be understood as representative only, and not limiting.

The following method relies on the detection of SNPs by the selective extension of only mismatched oligonucleotides. Phosphorylation of oligonucleotides inhibits or "blocks" the extension of 3' matched termini by DNA dependant DNA polymerases, consequently these blocked oligonucleotide probes are unable to act as primers of DNA polymerisation. However, in the presence of a proofreading DNA polymerase, the 3' mismatched nucleotide is cleaved from the oligonucleotide probe by the 3'-5' exonuclease activity of the enzyme, therefore allowing the 5'-3' polymerase activity to extend from the remaining annealed primer, resulting in the production of significant amounts of pyrophosphate. Since the cleavage of the 3' blocked nucleotide does not occur when the 3' termini of the oligonucleotide probe and sample are perfectly matched only mismatched SNP markers will produce a significant signal.

In this example, the signal of extension is the production of pyrophosphate (PPi), a by-product of the polymerisation reaction after the addition of each deoxynucleotide base. The PPi is converted to ATP by the enzymatic transfer of PPi to the adenosine 5' phosphosulfate substrate by the enzyme, ATP sulfurylase. The ATP product is converted to a detectable signal by the emission of photons from the action of luciferase.

It is important that the value of light produced from the reaction is direct from the polymerisation reaction and not due to background signal by the various components involved (eg. dATP can act as a substrate for luciferase). Consequently modified nucleotides such as deoxyadenosine thio-triphosphate (dATPαS) may be used.

Probes and Primers

Oligonucleotide probes and primers were synthesised by Genset Oligos (Singapore) and those containing 3'-terminal dideoxynucleotides were synthesised by Integrated DNA Technologies (USA).

| | | |
|---|---|---|
| M13F | GTT TTC CCA GTC ACG AC | [SEQ ID NO: 4] |
| M13R | GAG GAA ACA GCT ATG AC | [SEQ ID NO: 5] |
| M13R-Phos | GAG GAA ACA GCT ATG AC-Phosphate | [SEQ ID NO: 6] |
| M13mm | CAG GAA ACA GCT ATG AT | [SEQ ID NO: 7] |
| M13mm-Phos | GAG GAA ACA GCT ATG AT-Phosphate | [SEQ ID NO: 8] |

Reagents

A mixture of 0.06 U/mL adenosine 5'-triphosphate sulfurylase (E.C.: 2.7.7.4; #A 8957; Sigma, USA) and 5 μM adenosine 5'-phosphosulfate (#A 5508; Sigma, USA) was used as the final additive for the detection of pyrophosphate. The addition of this last reagent allows the conversion of PPi to ATP through the action of ATP sulfurylase on APS. The production of ATP is readily consumed by the action of luciferase to produce light that can be detected by the luminometer. The luciferase mixture containing Luciferin and Luciferase (#FF1000; Promega, Australia) was utilised for the detection of ATP. The extension reactions require the use of a DNA polymerase with no 3'-5' exonuclease activity such as Taq DNA Polymerase as well as a DNA polymerase with proofreading capability (3'-5' exonuclease activity). For the latter purpose, the Elongase enzyme mixture (# 10480-010; Life Technologies, Australia) was used. The enzyme contains a special mixture of Taq and Deep Vent (*Pyrococcus species* GB-D) DNA polymerase that can proofread 3' DNA mismatches and extend suitable primers at optimal activities. Template DNA was pGEM plasmid DNA (Promega) containing hybridisation sites for M13 forward and reverse oligonucleotides. Extension reactions were carried out using an Applied Biosystems 2400 Thermal Cycler according to the temperatures and times indicated in Table 13.

Detection of Pyrophosphate

Typically, 5 μL of sample to be assayed was placed into a well from a white 96-well plate (BMG, Australia). Plates were read using an EG&G Berthold Microlumat 96V (Berthold, Germany).

For the Berthold luminometer, each well was measured individually for 20 s, after which, 25 μL of APS mixture was read for a further 30 s. All additions and measurements were performed during shaking. The luminometer was set at a temperature of 25° C. Integrated measurements were taken from time points 7 s to 12 s (before reagent addition) and from 14 s to 19 s (after reagent addition). The two values were subtracted from each other and the final value used to evaluate whether extension has occurred. Kinetic measurement can also be involved to monitor the progress of the reaction.

Typically, the mixture of sulfurylase, sample and Luciferin/Luciferase reagent was assayed for 20 s at 0.5 s intervals. After which the addition of 25 μL of APS solution to the well and monitored for a further 30 s. There is a noticeable sharp increase in the light output from the reaction of conversion of APS to ATP by the sulfurylase enzyme. This method is useful when the kinetics of the reaction are to be monitored where a reaction showing a steady increase in output will produce false results than those with stable light output.

EXAMPLE 1

Determination of the Light Emission Activity of the Extension Reaction Components.

Reactions A-F as listed in Table 1 below were prepared and 5 μL of each reaction was assayed by addition to standard assay buffer and read immediately. The light output listed in Table 1 were blanked on the signal from ATP-free water blank and average from duplicate results of integrated signal output for 5 second integration. These results show that at least one of the added dNTP's are able to be used as a substrate for light production by luciferase.

TABLE 1

| Reaction | Component | Concentration | Volume (uL) | Relative Light Units (RLU) |
|---|---|---|---|---|
| A | Buffer | 10X | 0.6 | 69,800 |
| B | Enzyme | | 1 | 74,800 |
| C | DNA (pGEM) | 20 ng/uL | 5 | 52,800 |
| D | Oligonucleotide Primer/probe | 10 pmol/uL | 1 | 75,900 |
| E | DNTP | 2.5 mM ea. | 2.2 | 533,500 |
| F | DH$_2$O | — | 6 | 73,600 |

EXAMPLE 2

Contribution of Different dNTPs to Background Light Output

Previous studies have demonstrated that dATP can be used as a substrate by luciferase. To determine the contribution of background light output from dATP in this method, typical extension reaction conditions were reproduced (as per Table 1) with no incubation. Table 2 shows that by the exclusion of dATP in the reaction mixture, the background light output is decreased significantly.

TABLE 2

| Reaction | Condition | RLU |
|---|---|---|
| A | dATP, dCTP, dGTP, dTTP | 443,000 |
| B | dCTP, dGTP, dTTP | 268,000 |

EXAMPLE 3

Standardisation of Detection Limits for Pyrophosphate (PPi) Detection

To determine the effective concentration of PPi that the system could detect, reactions were set up with known concentrations of PPi. Approximately 5 μL of each PPi solution was added to standard assay solution and light output was determine using the EG&G Berthold Luminometer. Table 3 illustrates the average relative light output determined from duplicate reactions over the effective range of PPi concentration. High concentrations of PPi show significant inhibition of luciferase light production. The most accurate and sensitive detection of PPi concentration was determined to be between $10^{-6}$ and $10^{-7}$ M PPi.

TABLE 3

| PPi Conc (M) | RLU |
|---|---|
| $10^{-1}$ | 500 |
| $10^{-2}$ | 8,745,000 |
| $10^{-3}$ | 18,740,300 |
| $10^{-4}$ | 20,711,100 |
| $10^{-5}$ | 4,997,800 |
| $10^{-6}$ | 1,254,000 |
| $10^{-7}$ | 409,300 |
| $10^{-8}$ | 228,600 |

EXAMPLE 4

Extension of Oligonucleotide Primer by Tag DNA Polymerase.

Extension reactions with match and mismatch primers was conducted to determine the ability of Taq polymerase extension products to be detected using the Luciferase detection system (Table 4 and 5). Reactions were set up as per Table 11.

TABLE 4

| Reaction | Primer/probe | Control (RLU) | Extension (RLU) | Change (RLU) |
|---|---|---|---|---|
| A | 3' Match (M13F) | 22,000 | 133,000 | 111,000 |
| B | 3' Mismatch (M13 mm) | 36,000 | 40,000 | 4,000 |

It is clear from these results (Table 4) that polymerisation of matched oligonucleotide primers can be readily detected via an increase in RLU compared to the control samples which did not undergo extension reactions. It is also clear that Taq polymerase is also able to extend with reduced efficiency from a 3' mismatched primer.

Extension of a matched oligonucleotide primer (M13F) by Taq DNA Polymerase was performed in the presence of all deoxynucleotides (2.5 mM each) and also with the exception of dATP which was excluded in reaction B (Table 5). Reactions were set up essentially as per Table 1 except for the dNTP concentrations. The results of reaction A which was performed in the presence of all nucleotides showed a significant increase in light output after extension demonstrating that polymerisation has occurred. Reaction B, which lacked dATP had significantly lower background (see control), showed some extension of primer, however, not to the same extent as reaction A. This is likely to be because the primer could only be extended until a dATP was to be incorporated, resulting in less polymerisation.

TABLE 5

| Reaction | Condition | Control (RLU) | Extension (RLU) | Change (RLU) |
|---|---|---|---|---|
| A | dATP, dCTP, dGTP, dTTP | 443,000 | 1,498,000 | 1,055,000 |
| B | dCTP, dGTP, dTTP | 268,000 | 323,000 | 55,000 |

EXAMPLE 5

Extension of Oligonucleotide Primers From Blocked 3' Match and Mismatch Probes by Tag DNA Polymerase To determine the extent to which the phosphate blocking of the 3' end of the oligonucleotide probe would inhibit extension by Taq polymerase reactions with blocked match and mismatch probes were set up (Table 6). Reactions were set up as per Table 11.

TABLE 6

| Reaction | Primer/probe | Contol (RLU) | Extension (RLU) | Change (RLU) |
|---|---|---|---|---|
| A | 3' Blocked Match (M13R-Phos) | 47,000 | 37,000 | −10,000 |
| B | 3' Blocked Mismatch (M13 mm-Phos) | 37,783 | 34,374 | −3,009 |

From the results in Table 6 it can be seen that the phosphate group linked to the 3' end of the oligonucleotide probe is able to efficiently inhibit extension by Taq polymerase.

EXAMPLE 6

Examination of Signal (RLU) from Multiple Cycles of Extension.

To determine whether more than one round of extension would produce a significantly increase in the amount of pyrophosphate released during extension, reactions were performed where after each extension round, the amount of pyrophosphate was determined. Reactions were set up as for Table 11 using Taq polymerase and primer M13F. Table 7 shows the increase in pyrophosphate produced after each extension round where reactions B and C lacked the addition of primer and DNA template respectively. After 3 extension rounds, the concentration of pyrophosphate was significantly greater than the unextended reaction. No significant change in signal was produced by controls without primer or DNA. These results demonstrate that after only one round of extension sufficient pyrophosphate is released for ready detection using the luciferase ATP detection method. However, by using multiple rounds of extension from the primer, the sensitivity of the assay can be greatly increased.

TABLE 7

| Reaction | Extension Rounds (RLU) | | | |
|---|---|---|---|---|
| | 0 | 1 | 2 | 3 |
| A | 22,000 | 31,000 | 56,000 | 148,000 |
| B | 20,000 | 23,000 | nt | 27,000 |
| C | 18,000 | nt | nt | 23,000 |

EXAMPLE 7

Extension of Oligonucleotide Primers From 3' Match and Mismatch Primers by Elongase Enzyme Mix.

To determine the effect of using an enzyme mix with proof-reading capability, the Elongase enzyme was used in extension reactions using match and mismatch probes. Table 8 shows extension of the match probe (Reaction A) and significantly less efficient extension of mismatched probe (Reaction B).

TABLE 8

| Reaction | Primer/probe | Control (RLU) | Extension (RLU) | Change (RLU) |
|---|---|---|---|---|
| A | 3' Match (M13F) | 64,000 | 380,000 | 316,000 |
| B | 3' Mismatch (M13 mm) | 65,000 | 156,000 | 91,000 |

EXAMPLE 8

Extension of Oligonucleotide Probes With and Without 3'-end Phosphate Blockage by Elongase Enzyme Mix The ability to block extension of oligonucleotide probes by the addition of 3'-phosphate groups was investigated. Extension was only seen for the unblocked match primer (Reaction A) and not significant extension was observed for the blocked match primer (Reaction B) (Table 9). This result confirms that Elongase is unable to efficiently extend from a 3' matched probe which is 3' blocked.

TABLE 9

| Reaction | Primer/probe | Control (RLU) | Extension (RLU) | Change (RLU) |
|---|---|---|---|---|
| A | 3' Match (M13F) | 64,000 | 380,000 | 316,000 |
| B | 3' Blocked Match (M13R-phos) | 66,000 | 78,000 | 12,000 |

EXAMPLE 9

Extension of 3'-phosphate Blocked Oligonucleotide Probes With and Without 3'-end Mismatch by Elongase Enzyme Mix Given the ability to block extension of probes by the addition of a 3' phosphate group (Table 9), reactions were set up to illustrate the effect of a blocked mismatch primer. Table 10 shows significant extension was observed for the 3' blocked mismatch primer and no significant extension was observed for the 3' blocked match primer. It is clear that the ability of the Elongase polymerase mix with proofreading activity can recognise the mismatch and is able to cleave the 3' mismatch and blocked nucleotide from the primer and then able to extend from the perfectly matched remaining primer. There is a clear distinction shown between blocked match and blocked mismatch primers.

TABLE 10

| Reaction | Primer | Control | Extension | Change |
|---|---|---|---|---|
| A | Blocked Match (M13R-Phos) | 66,000 | 78,000 | 12,000 |
| B | Blocked Mismatch (M13 mm-Phos) | 64,000 | 602,000 | 538,000 |

EXAMPLE 10

Protocol for Assay of Pyrophosphate Detection from Extension Reactions

The following Table 10 shows the reactions required for Taq DNA polymerase reaction:

TABLE 11

| Reagent | Stock Conc. | Volume Used (µL) | Final Conc. |
|---|---|---|---|
| MgCl2 | 25 mM | 1.5 | 1.5 mM |
| dNTPs | 50 µM ea. | 2.5 | 5 µM ea. |
| Buffer A | 10X | 2.5 | 1X |
| Enzyme | 5.5 U/µL | 0.2 | 44 mU/µL |
| Primer | 10 pmol/µL | 1 | 0.4 pmol/µL |
| DNA (pGEM) | 0.2 µg/µL | 0.5 | 4 ng/µL |
| dH$_2$O | — | 15.5 | — |
| Total | | 25 | |

Table 12 shows the set up for the extension reaction for Elongase.

TABLE 12

| Reagent | Stock Conc. | Volume Used (µL) | Final Conc. |
|---|---|---|---|
| dNTPs | 50 µM ea. | 2.5 | 5 µM ea. |
| Buffer A | 5X | 2.5 | 0.5X |
| Buffer B | 5X | 2.5 | 0.5X |
| Enzyme Mix | Not Provided | 0.5 | ? |
| Primer | 10 pmol/µL | 1 | 0.4 pmol/µL |
| DNA (pGEM) | 0.2 µg/µL | 0.5 | 4 ng/µL |
| dH$_2$O | — | 15.5 | — |
| Total | | 25 | |

Buffer A and buffer B referred to in Table 11 and Table 12 contain different concentrations of magnesium ions and can be adjusted. The final concentration using the above protocols was 1.5 mM Magnesium ions.

The reaction tubes were place into the thermocycler and the following incubation times as shown in Table 13 below, were used for the extension reactions for the number of rounds desired.

TABLE 13

| Temperature (° C.) | Time (mm:ss) |
|---|---|
| 94 | 2:00 |
| 94 | 0:30 |
| 48 | 0:20 |
| 72 | 0:45 |

Control tubes were placed on ice until assayed for pyrophoshate acitivity by luminometry.

Modifications and variations such as would be apparent to the skilled address are considered to fall within the scope of the present invention.

The invention claimed is:

1. A method of determining whether a nucleotide at a target position in a single-stranded sample DNA sequence is complementary to the nucleotide on the 3' end of an oligonucleotide probe, which comprises:
   (i) providing the oligonucleotide probe, wherein the nucleotide on the 3' end of said oligonucleotide probe is a terminally blocked nucleotide such that 5'-3' extension of said oligonucleotide probe cannot take place in the presence of said blocked nucleotide, and wherein said oligonucleotide probe is capable of hybridizing to said single-stranded sample DNA sequence;
   (ii) incubating said single-stranded sample DNA sequence with said oligonucleotide probe in the presence of (a) a DNA polymerase having 3'-5' exonuclease activity and (b) nucleotide triphosphates, under conditions that allow hybridization of the oligonucleotide probe to the single-stranded sample DNA sequence, without PCR amplification, such that, when said blocked nucleotide of said oligonucleotide probe is complementary to the nucleotide at said target position of said single-stranded sample DNA sequence, said blocked nucleotide of said oligonucleotide probe and the nucleotide at said target position of said single-stranded sample DNA sequence form a base pair and said blocked nucleotide of said oligonucleotide probe is not cleaved from said oligonucleotide probe by the 3'-5' exonuclease activity of said DNA polymerase; and when said blocked nucleotide of said oligonucleotide probe is not complementary to the nucleotide at said target position of said single-stranded sample DNA sequence, said blocked nucleotide of said oligonucleotide probe is cleaved from said oligonucleotide probe by the 3'-5' exonclease activity of the said DNA polymerase, thereby allowing the 5'-3' extension of said oligonucleotide probe and producing pyrophosphate; and
   (iii) detecting the cleavage of said blocked nucleotide of said oligonucleotide probe by detecting said pyrophosphate wherein the presence of said cleavage indicates that said nucleotide at said target position of a said single-stranded sample DNA sequence is not complementary to the nucleotide on the 3' end of said oligonucleotide probe.

2. The method according to claim 1, wherein said DNA polymerase is a DNA dependent DNA polymerase.

3. The method according to claim 2, wherein the detection of said pyrophosphate comprises contacting the pyrophosphate with reagents for converting the pyrophosphate to adenosine triphosphate (ATP) and detecting the presence of the ATP.

4. The method according to claim 3, wherein the presence of the ATP is detected by contacting the ATP with luciferase and luciferin, and measuring light produced by hydrolyzing the ATP.

5. The method according to claim 4, wherein the light is detected by an optical detection device.

6. The method according to claim 1, wherein the nucleotide on the 3' end of the oligonucleotide probe is blocked by phosphate or dideoxy moieties bound thereto.

7. The method according to claim 1, further comprising providing two or more oligonucleotide probes which hybridize to said single-stranded sample DNA sequence wherein the nucleotide on the 3' end of each of said two or more oligonucleotide probes is different.

8. The method according to claim 1, wherein the oligonucleotide probe is immobilized on a solid phase.

9. The method according to claim 1, further comprising repeating steps (i)-(iii) using another probe, wherein said another probe hybridizes to said single-stranded sample DNA sequence, wherein the nucleotide on the 3' end of said another probe is different from the nucleotide on the 3' end of said oligonucleotide probe and wherein said oligonucleotide probe and said another probe are immobilized on a solid phase.

10. The method according to claim 9, wherein said oligonucleotide probe and said another probe are located on a discrete array on the solid phase.

11. The method according to claim 1, wherein said oligonucleotide probe further comprises a fluorescent moiety and a quencher moiety, wherein the fluorescent moiety or the quencher moiety, but not both, is attached to the nucleotide on the 3' end of said oligonucleotide probe, and wherein step (iii) further comprises detecting an increase in fluorescence wherein the fluorescence is generated from the fluorescent moiety and the increase in fluorescence is due to separation of the fluorescent moiety from the quencher moiety based on said cleavage of said blocked nucleotide of said oligonucleotide probe.

* * * * *

SEQUENCE LISTING

<160> NUMBER OF SEQ ID NOS: 8

<210> SEQ ID NO 1
<211> LENGTH: 43
<212> TYPE: DNA
<213> ORGANISM: Artificial Sequence
<220> FEATURE:

<223> OTHER INFORMATION: Sample DNA strand

<400> SEQUENCE: 1
aaatgcttgt acacaaagct agtctagcga aggttgctaa ctc                43

<210> SEQ ID NO 2
<211> LENGTH: 18
<212> TYPE: DNA
<213> ORGANISM: Artificial Sequence
<220> FEATURE:
<223> OTHER INFORMATION: Match probe

<400> SEQUENCE: 2
ctagactagc tttgtgta                                            18

<210> SEQ ID NO 3
<211> LENGTH: 18
<212> TYPE: DNA
<213> ORGANISM: Artificial Sequence
<220> FEATURE:
<223> OTHER INFORMATION: Mismatch probe

<400> SEQUENCE: 3
ctagactagc tttgtgtg                                            18

<210> SEQ ID NO 4
<211> LENGTH: 17
<212> TYPE: DNA
<213> ORGANISM: Artificial Sequence
<220> FEATURE:
<223> OTHER INFORMATION: M13F

<400> SEQUENCE: 4
gttttcccag tcacgac                                             17

<210> SEQ ID NO 5
<211> LENGTH: 17
<212> TYPE: DNA
<213> ORGANISM: Artificial Sequence
<220> FEATURE:
<223> OTHER INFORMATION: M13R

<400> SEQUENCE: 5
caggaaacag ctatgac                                             17

<210> SEQ ID NO 6
<211> LENGTH: 17
<212> TYPE: DNA
<213> ORGANISM: Artificial Sequence
<220> FEATURE:
<223> OTHER INFORMATION: M13R-Phos
<220> FEATURE:
<221> NAME/KEY: misc_feature
<222> LOCATION: (17)..(17)
<223> OTHER INFORMATION: Phosphorylation

<400> SEQUENCE: 6
caggaaacag ctatgac                                             17

<210> SEQ ID NO 7
<211> LENGTH: 17
<212> TYPE: DNA
<213> ORGANISM: Artificial Sequence
<220> FEATURE:
<223> OTHER INFORMATION: M13mm

<400> SEQUENCE: 7

```
caggaaacag ctatgat                                                    17

<210> SEQ ID NO 8
<211> LENGTH: 17
<212> TYPE: DNA
<213> ORGANISM: Artificial Sequence
<220> FEATURE:
<223> OTHER INFORMATION: M13mm-Phos
<220> FEATURE:
<221> NAME/KEY: misc_feature
<222> LOCATION: (17)..(17)
<223> OTHER INFORMATION: Phosphorylation

<400> SEQUENCE: 8
caggaaacag ctatgat                                                    17
```